United States Patent [19]

Samochocka et al.

[11] Patent Number: 4,921,944
[45] Date of Patent: May 1, 1990

[54] METHOD OF PHARMACEUTIC PRODUCTION

[75] Inventors: Krystyna Samochocka; Janusz J. Szymendera, both of Warsaw, Poland

[73] Assignee: Uniwersytet Warszawski, Warsaw, Poland

[21] Appl. No.: 223,792

[22] Filed: Jul. 25, 1988

Related U.S. Application Data

[63] Continuation-in-part of Ser. No. 55,550, May 27, 1987, abandoned.

[30] Foreign Application Priority Data

Jun. 10, 1986 [PL] Poland ................... 259998

[51] Int. Cl.$^5$ .......................... C07F 5/00; A61K 49/02
[52] U.S. Cl. ...................................... 534/10; 424/1.1; 556/136
[58] Field of Search ............... 534/10, 15, 16; 424/1.1; 556/136

[56] References Cited

U.S. PATENT DOCUMENTS 3,663,688  5/1972  Grotenhuis .................... 424/1.1

OTHER PUBLICATIONS

Gummin, D. D. et al, "Variable-Temperature $^{195}$Pt NMR Spectroscopy", Inorg. Chem., vol. 25, No. 14, 7/2/86, pp. 2429–2433.
Mogilevkina et al, "Reaction of Dichloro(ethylenediamine)platinum with Methionine", Russ. J. Inorg. Chem., 1980, 25, pp. 581–583.

Primary Examiner—John S. Maples
Attorney, Agent, or Firm—Ladas & Parry

[57] ABSTRACT

The object of the invention is a method for preparing a compound of formula I

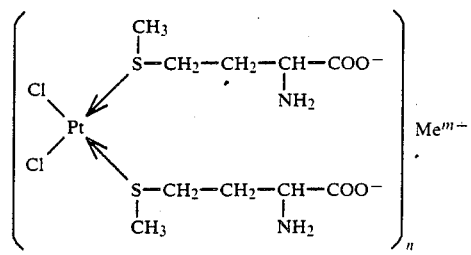

wherein Me$^{m+}$ is a lanthanide and n is a number from 1–3, is used for diagnosis of neoplasms. The compound is prepared by adding an aqueous solution of hydrazide hydrochloride to potassium hexachloroplatinate, the suspension is mixed about two hours at 50° to 60° C. then about 30 minutes at 80° to 90° C., and upon cooling the reaction mixture, the unreacted potassium hexachloroplatinate is separated, the solution is decanted and filtered, and the pH of the filtrate is brought to 3 to 5. Methionine is then added in a molar ratio of methionine to tetrachloroplatinate of 2:1–4:1 and upon careful mixing for about 30 minutes a metal salt is added and preferably ytterbium chloride, and tagged with Yb$^{-169}$. The components are then mixed and the pH of the solution is brought to 4–6.5 and filtered through a sterile filter.

5 Claims, No Drawings

METHOD OF PHARMACEUTIC PRODUCTION

This is a continuation-in-part of Ser. No. 07/055,550 filed on May 27, 1987, now abandoned.

BACKGROUND OF THE INVENTION

The object of the invention is a method for production of a compound designed for diagnosis of neoplasms.

The first metallic compound known for utilization in chemotherapy for diagnosis of neoplasms was a platinum inorganic compound, called "cis-platinum", or diaminodichloroplatinum, and was discovered in 1968 by Rosenberger.

Also known is an inorganic, radioactive platinum compound, $^{195}$Pt-cis-platinum and the method of producing it.

The disadvantages of these radioactive platinum compounds, for use as radiopharmaceutics, particularly for diagnosising neoplasms, results from the fact that they have a very short life of the isotope, amounting to only 4 days. The process for manufacturing them is complicated and in spite of the minimal doses utilized have a high toxicity.

As shown in animal studies the higher doses equal to 2.5 mg/kg caused pathological effects.

Also known is the method for producing dimethionineplatinum wherein to an aqueous solution of potassium tetrachloroplatinate, methionine is added in a molar ratio of 2 to 1 of methionine to tetrachloroplatinate, the mixture heated for 5 minutes, resulting in a chelated compound of dimethionineplatinum in which a platinum atom is coordinated by sulphur and nitrogen atoms.

The compound of dimethioneplatinum has not been previously used for producing pharmaceutics. The disadvantage of the application of this known method for pharmaceutic production, results from the fact, that the compound contains cyclic ligands.

SUMMARY OF THE INVENTION

The essence of the invention is based on the fact that a change in the process of preparing dichlorodimethionine-platinum, as in formula I

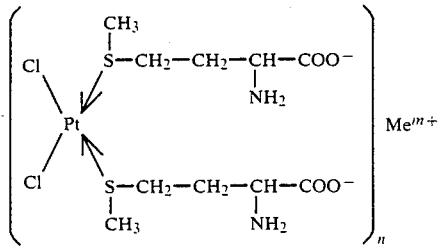

FORMULA I wherein Me$_m$$^+$ is a salt of a lanthanide, that is, one of La, Ce, Pr, Nd, Pm, Sm, Er, Gd, Tb, Dy, Ho, Eu, Tm, Yb and Lu, and n is a number from 1 to 3, preferably 2 produces a compound which contains non-cyclic ligands. It was shown, unexpectedly, that it's toxicity and mutagenicity is very low and upon tagging by metal salts, particularly by ytterbium$^{-169}$ chloride it shows an affinity for neoplastic tissues and provides very good results in scintigraphic examinations.

DETAILED DESCRIPTION OF THE INVENTION

The method for production of the compound according to the invention, involves adding an aqueous solution of hydrazide hydrochloride in the quantity of 96% of the calculated stoichiometric value to potassium hexachoroplatinate. The reaction suspension is mixed with an electromagnetic mixer, for about two hours at 50° to 80°, and then for about 30 minutes at 80° to 90° C. Upon cooling of the reaction mixture, the unreacted potassium hexachloroplatinate is separated by centrifugation, the solution is decanted and filtered through glass wool or Milipore and the pH of the filtrate is brought to 3 to 5 by a solution of 0.3N NaOH. Next, to the obtained tetrachloroplatinate, methionine is added with continuous mixing in a molar ratio of methionine to tetrachloroplatinate 2:1, or more, particularly 2:1 to 4:1. Upon careful mixing for about 30 minutes, the dichlorodimethionineplatinum complex is purified on a chromatographic column. A metal salt is added, to the purified dichlorodimethionineplatinum complex, preferably the chloride of radioactive ytterbium$^{-169}$. The components are mixed for 5 to 10 minutes and the pH of the solution is brought to 4-6.5. The solution is filtered through a sterile filter and the product is ready for administration.

The advantage of manufacturing the pharmaceutic according to the process of the invention is the very low toxicity and mutagenicity of the compound prepared in this way. The LD$_{50}$ for a mouse for dichlorodi-D-methionineplatinum is 571 mg/kg. Some metal radionuclides, and particularly Yb$^{-169}$ have good radioactive characteristics and proper biological and physical properties. I.E. the radiation energy of gamma Yb$^{-169}$, is 60 to 300 kev, and the time for a half life—32 days. These characteristics provide good parameters of the radionuclide for scintigraphic examinations.

The metals make a stable complex with dichlorodimethionineplatinum, which are purged from the system of the animal with its urine. The retention of the Yb$^{-169}$ complex in the organism of the animals under examination is from 3 to 6% after 24 hours, and up to 3% after 72 hours. The relatively long half life of $^{169}$Yb provides the possibility of carrying out examinations for longer time intervals and yet also decreases the radiation load on the organism.

EXAMPLE I 96 ul of an aqueous one percent solution of hydrazide hydrochloride was added to 10 milligrams of potassium hexachloroplatinate. The reaction mixture was heated in the water bath at 50° to 60° C. for two hours while being continuously mixed with a magnetic mixer. The temperature is then increased to 85° C. for a period of 30 minutes. Upon cooling, the unreacted potassium hexachloroplatinate was separated by centrifugation. The solution was decanted and filtered through glass wool. The pH of the solution was brought to about 4, with a solution of 0.3N NaoH 5.4 milligrams of D-methionine were then added, with careful mixing, for about 30 minutes, the complex of dichlorodi-D-methionineplatinum was purified and an 100 ul solution of NaCl, physiological salt, was added, as well as 100 ul of ytterbium chloride tagged with Yb$^{-169}$ with an activity of 1 mCi, i.e. 37 MBq. The reaction mixture was brought to a pH of about 6,5 with 0.3N NaOH. It has been ascertained that the solution is stable if stored at a temperature of +4° C.

For biological examination of mice, 40 ul of the above mentioned solution per mouse were intravenously injected. The biodistribution among the control animals and the mice inoculated with particular tumors is presented in tables 1 and 2.

EXAMPLE II 96 ul of an aqueous one percent solution of hydrazide hydrochloride was added to 10 milligrams of potassium hexachloroplatinate. The reaction mixture was heated in the water bath at 50° to 60° C. for two hours while being continuously mixed with a magnetic mixer. The temperature is then increased to 85° C. for a period of 30 minutes. Upon cooling, the unreacted potassium hexachloroplatinate was separated by centrifugation. The solution was decanted and filtered through glass wool. The pH of the solution was brought to about 4, with a solution of 0.3N NaOH. 8 milligrams of D-methionine were then added, with careful mixing, for about 30 minutes. The complex of dichlorodi D-methionineplatinum was purified and an 100 ul solution of NaCl, physiological salt, was added, as well as 100 ul of thulium chloride tagged with Tm-167 with an activity of 1 mCi, i.e. 37 MBq. This reaction mixture was brought to a pH of about 5 with 0.3N NaOH. It has been ascertained that the solution is stable if stored at a temperature of +4° C. For biological examination of mice, 40 ul of the above mentioned solution per mouse were intravenously injected.

EXAMPLE III 96 ul of an aqueous one percent solution of hydrazide hydrochloride was added to 10 milligrams of potassim hexachloroplatinate. The reaction mixture was heated in the water bath at 50° to 60° C. for two hours while being continuously mixed with a magnetic mixer. The temperature is then increased to 85° C. for a period of 30 minutes. Upon cooling, the unreacted potassium hexachloroplatinate was separated by centrifugation. The solution was decanted and filtered through glass wool. The pH of the solution was brought to about 4, with a solution of 0.3N NaOH. 9 milligrams of D-methionine were then added, with careful mixing, for about 30 minutes, the complex of dichlorodi-D-methionineplatinum was purified and an 100 ul solution of NaCl, physiological salt, was added, as well as 100 ul of terbium chloride tagged with Tb-153 with an activity of 1 mCi, i.e. 37 MBq. The reaction mixture was brought to a pH of about 6.5 with 0.3N NaOH. It has been ascertained that the solution is stable if stored at a temperature of +4° C. For biological examination of mice, 40 ul of the above mentioned solution per mouse were intravenously injected.

It has been ascertained that the solution is stable if stored at a temperature of 4° C. For biological examination of mice 40 ul of the above mentioned solution per mouse were intravenously injected.

TABLE 1

Biodistribution among BALB control mice and mice inoculated with Ehrlich neoplasms

| Organ | Upon 24 hours | | upon 72 hours | |
|---|---|---|---|---|
| | control | neoplasm | control | neoplasm |
| liver | 0.08 | 0.08 | 0.07 | 0.06 |
| spleen | 0.03 | 0.03 | 0.07 | 0.03 |
| kidneys | 0.45 | 0.43 | 0.27 | 0.30 |
| lungs | 0.02 | 0.02 | 0.03 | 0.02 |
| bone | 0.18 | 0.15 | 0.22 | 0.23 |
| blood | 0.004 | 0.005 | 0.002 | 0.002 |
| muscle | 0.03 | 0.03 | 0.01 | 0.01 |
| neoplasm | — | 0.07 | — | 0.07 |
| neoplasm/blood | — | 14 | — | 35 |
| neoplasm/muscle | — | 2.3 | — | 7 |
| retention | 6.3% | 3.0% | 5.6% | 3.9% |

TABLE 2

Biodistribution among B-10 control mice and inoculated with leukemic neoplasms.

| Organ | upon 24 hours | |
|---|---|---|
| | control | with neoplasm |
| liver | 0.06 | 0.07 |
| spleen | 0.02 | 0.02 |
| kidneys | 0.37 | 0.39 |
| lungs | 0.02 | 0.01 |
| bone | 0.16 | 0.09 |
| blood | 0.002 | 0.003 |
| muscle | 0.006 | 0.002 |
| neoplasm | — | 0.06 |
| neoplasm/blood | — | 20 |
| neoplasm/muscle | — | 30 |
| retention | 6% | 5.5% |

We claim:
1. A method for producing a compound for use in the diagnosis of tumors comprising:
    (a) adding methionine to a solution of sodium chloride and tetrachloroplatinate in a molar ratio of tetrachloroplatinate to methionine of 2:1–4:1,
    (b) thoroughly mixing the mixture of (a) for about 30 minutes,
    (c) purifying the resulting dichlorodimethionineplatinate,
    (d) adding a radioactive lanthanide salt,
    (e) mixing the components (c) and (d),
    (f) bringing the solution of (e) to a pH of about 6.5, and (g) filtering the solution with a filter.
2. The method, as in claim 1 wherein the dichlorodimethioninepalatinate is purified on a chromatographic column.
3. The method, as in claim 1 wherein the lanthanide is selected from the group consisting of ytterbium, thulium and terbium.
4. The method, as in claim 3 wherein the filter is a sterile filter.
5. The method, as in claim 3 wherein the tetrachloroplatinate is prepared by (a) adding an aqueous solution of hydrazide hydrochloride to potassium hexachloroplatinate (b) heating the solution at 50°–80° C. with mixing, (c) increasing the temperature to about 80°–90° C., (d) cooling the mixing of (c), (e); separating off the unreacted potassium hexachloroplatinate, and (f) bringing the pH to 3–5.

* * * * *